United States Patent [19]

Usui et al.

[11] Patent Number: 4,830,843
[45] Date of Patent: May 16, 1989

[54] SYNTHETIC LAMELLAR MAGNESIUM PHYLLOSILICATE AND PROCESS FOR PREPARATION THEREOF

[75] Inventors: Koichi Usui, Hoya; Teiji Sato; Masanori Tanaka, both of Shibata; Noriyuki Takahashi, Nakajo, all of Japan

[73] Assignee: Mizusawa Industrial Chemicals, Ltd., Tokyo, Japan

[21] Appl. No.: 4,215

[22] Filed: Jan. 5, 1987

Related U.S. Application Data

[63] Continuation of Ser. No. 747,233, Jun. 21, 1985, abandoned.

[30] Foreign Application Priority Data

Jun. 22, 1984 [JP] Japan ................... 59-127568

[51] Int. Cl.$^4$ ............ C01B 33/24; C01B 33/20; B01J 13/00; B01J 21/16
[52] U.S. Cl. ................. 423/331; 252/315.5; 423/326; 502/84; 502/251
[58] Field of Search .......... 423/326, 327, 328, 328 T, 423/329, 331, 332; 502/63, 251; 501/84

[56] References Cited

U.S. PATENT DOCUMENTS

| | | | |
|---|---|---|---|
| 2,773,843 | 12/1956 | Kimberlin, Jr. et al. | 502/251 |
| 3,264,130 | 8/1966 | Mays | 423/331 |
| 3,844,979 | 10/1974 | Hickson | 423/331 |
| 4,049,780 | 9/1977 | Neumann | 423/326 |
| 4,405,371 | 9/1983 | Sugahara et al. | 106/21 |
| 4,499,320 | 2/1985 | Garces | 423/326 |
| 4,542,002 | 9/1985 | Corma et al. | 423/331 |

FOREIGN PATENT DOCUMENTS 666992 7/1963 Canada ................... 423/331
53-123421 10/1978 Japan ................... 423/331

Primary Examiner—Gary P. Straub
Attorney, Agent, or Firm—Sherman and Shalloway

[57] ABSTRACT

A synthetic lamellar magnesium phyllosilicate has as the main component a composition represented by the following formula:

$$Mg_3Si_4O_{10}(OH)_2 \cdot nH_2O \tag{1}$$

wherein n is a number of up to 5, and has X-ray diffraction peaks at spacings of 4.5–4.6 Å, 2.5–2.6 Å and 1.5–1.6 Å, wherein the lamination asymmetry index (Is) defined by the following formula:

$$Is = \tan\theta_2 / \tan\theta_1 \tag{2}$$

wherein
$\theta_1$ stands for the angle formed by the peak perpendicular and the peak tangent on the small diffraction angle side in said X-ray diffraction peak at a spacing of 4.5–4.6 Å, and
$\theta_2$ stands for the angle formed by the peak perpendicular and the peak tangent on the large diffraction angle side in said X-ray diffraction peak, is at least 3.0, the BET specific surface area is at least 300 m$^2$/g and the Methylene Blue decolorizing power (JIS K-1470) is at least 100 ml/g. This synthetic lamellar magnesium phyllosilicate is prepared by a process comprising subjecting active silicic acid or active aluminosilicic acid and an oxide or hydroxide of magnesium or a compound capable of forming said oxide or hydroxide under reaction conditions to a hydrothermal treatment.

8 Claims, 2 Drawing Sheets

SYNTHETIC LAMELLAR MAGNESIUM PHYLLOSILICATE AND PROCESS FOR PREPARATION THEREOF

This application is a continuation of application Ser. No. 747,233, filed June 21, 1985, now abandoned.

BACKGROUND OF THE INVENTION (1) Field of the Invention

The present invention relates to synthetic lamellar magnesium phyllosilicate and a process for the preparation thereof. More particularly, the present invention relates to a process for preparing synthetic lamellar magnesium phyllosilicate having a good emulsifying property and a large specific surface area and being excellent in the adsorbing property from active silicic acid or active aluminosilicic acid obtained by an acid treatment of a clay mineral.

(2) Description of the Prior Art

It is known that various magnesium silicate minerals may be synthesized by hydrothermal reaction of starting materials of the $MgO$-$SiO_2$-$H_2O$ system. For example, it is reported in Journal of the American Ceramic Society, 43, No. 10, pages 542–549 (1960) that when a starting material such as a coprecipitate having a composition of $3MgO$-$4SiO_2$ is subjected to a hydrothermal treatment at 282° C. under a pressure of 950 psi for 168 hours, magnesium silicate having a talc type crystal structure is formed, and that if a starting material having a composition of $3MgO$-$2SiO_2$ is subjected to a hydrothermal treatment at 155° C. under a pressure of 65 psi for 432 hours, a scaly serpentine type crystal is formed and if the same starting material is subjected to a hydrothermal treatment at 282° C. under a pressure of 950 psi for 168 hours, a crysotile type crystal is formed. This research is important in that synthesis of magnesium silicate minerals has become possible. However, the minerals prepared according to this proposal have a small specific surface area and a low adsorbing property and are still insufficient in the utility.

Recently, Japanese Patent Application Laid-Open Specification No. 9812/83 proposes a process in which lowly crystalline magnesium silicate hydrate is prepared by subjecting an amorphous silicic acid starting material such as ferrosilicon dust, a magnesium oxide starting material and an aqueous slurry starting material to a hydrothermal treatment under a pressure lower than 9 kg/cm², and it is taught that if amorphous silica such as white carbon is used as the starting material, the water repellency of the obtained magnesium silicate is low.

SUMMARY OF THE INVENTION

We found that if active silicic acid or active aluminosilicic acid obtained by an acid treatment of a clay material is selected among various silicic acid starting materials and is subjected to a hydrothermal treatment together with a starting magnesium material, synthetic lamellar magnesium phyllosilicate having a peculiar emulsifying property, a large specific surface area and a high adsorbing property is obtained.

It also was found that the synthetic lamellar magnesium phyllosilicate obtained according to the above process has a peculiar laminate structure and this laminate structure has important influences on the properties of the magnesium phyllosilicate.

More specifically, in accordance with the present invention, there is provided synthetic lamellar magnesium phyllosilicate, which has as the main component a composition represented by the following formula:

$$Mg_3Si_4O_{10}(OH)_2 \cdot nH_2O \qquad (1)$$

wherein n is a number of up to 5, and has X-ray diffraction peaks at spacings of 4.5–4.6 Å, 2.5–2.6 Å and 1.5–1.6 Å, wherein the lamination asymmetry index (Is) defined by the following formula:

$$Is = \tan\theta_2 / \tan\theta_1 \qquad (2)$$

wherein $\theta_1$ stands for the angle formed by the peak perpendicular and the peak tangent on the small diffraction angle side in the X-ray diffraction peak at a spacing of 4.5–4.6 Å, and $\theta_2$ stands for the angle formed by the peak perpendicular and the peak tangent on the large diffraction angle side in said X-ray diffraction peak, is at least 3.0, the BET specific surface area is at least 300 m²/g and the Methylene Blue decolorizing power (JIS K-1470) is at least 100 ml/g.

Furthermore, in accordance with the present invention, there is provided a process for the preparation of synthetic lamellar magnesium phyllosilicate, which comprises subjecting active silicic acid or active aluminosilicic acid and an oxide or hydroxide of magnesium or a compound capable of forming said oxide or hydroxide under reaction conditions to a hydrothermal treatment.

DETAILED DESCRIPTION OF THE PREFERRED EMBODIMENTS

The present invention will now be described in detail.

Structure and Characteristics of Synthetic Lamellar Magnesium Phyllosilicate The synthetic lamellar magnesium phyllosilicate of the present invention has as the main component a chemical composition represented by the following formula:

$$Mg_3Si_4O_{10}(OH)_2 \cdot nH_2O \qquad (1)$$

The number (n) of hydration water is up to 5 and preferably from 0.5 to 3. This synthetic lamellar magnesium phyllosilicate has as the main structure a three-layers structure comprising two layers of a tetrahedron of $SiO_4$ and one layer of an octahedron of $MgO_6$ sandwiched therebetween, and a two-layers structure comprising a layer of a tetrahedron of $SiO_4$ and a layer of an octahedron of $MgO_6$ may be contained so far as the essence of the three-layers structure is not lost. Moreover, an unreacted silica component or magnesia component may be contained, so far as the phyllosilicate has the properties described below.

Figure 1:
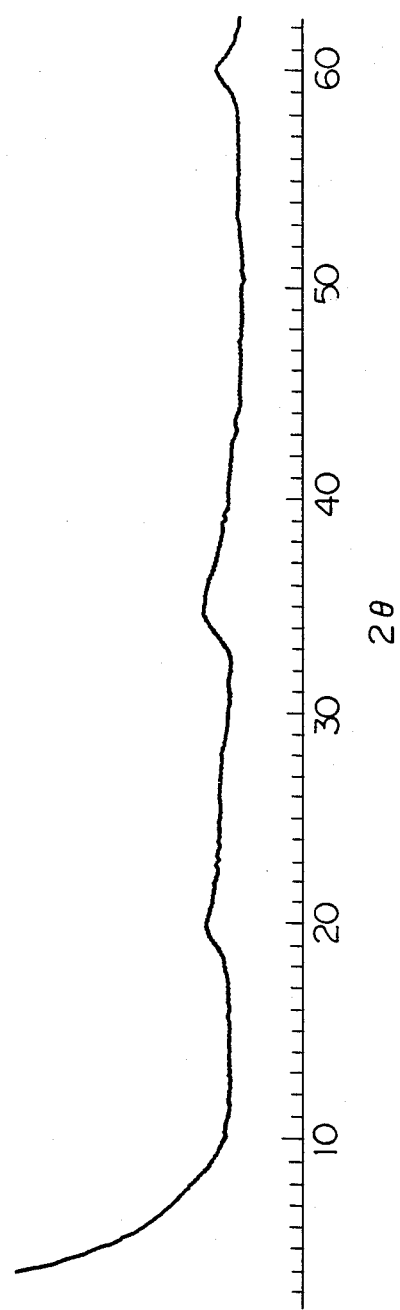
FIG. 1 shows an X-ray diffraction spectrum by Cu-Kα rays of synthetic lamellar magnesium phyllosilicate prepared in Example 1 of the present invention.

The synthetic lamellar magnesium phyllosilicate of the present invention has an X-ray diffraction pattern inherent to the above-mentioned layer structure. FIG. 1 of the accompanying drawings shows an X-ray diffraction spectrum by Cu-Kα rays of the synthetic lamellar magnesium phyllosilicate of the present invention. From FIG. 1, it is seen that the synthetic lamellar magnesium phyllosilicate of the present invention has diffraction peaks at a spacing of 4.5–4.6 Å (corresponding to planes (020) and (110)), a spacing of 2.5–2.6 Å (corresponding to plane (200)) and a spacing of 1.5–1.6 Å (corresponding to plane (060)). These X-ray diffraction peaks are common to natural trioctahedral type lamellar clay minerals.

Figure 2:
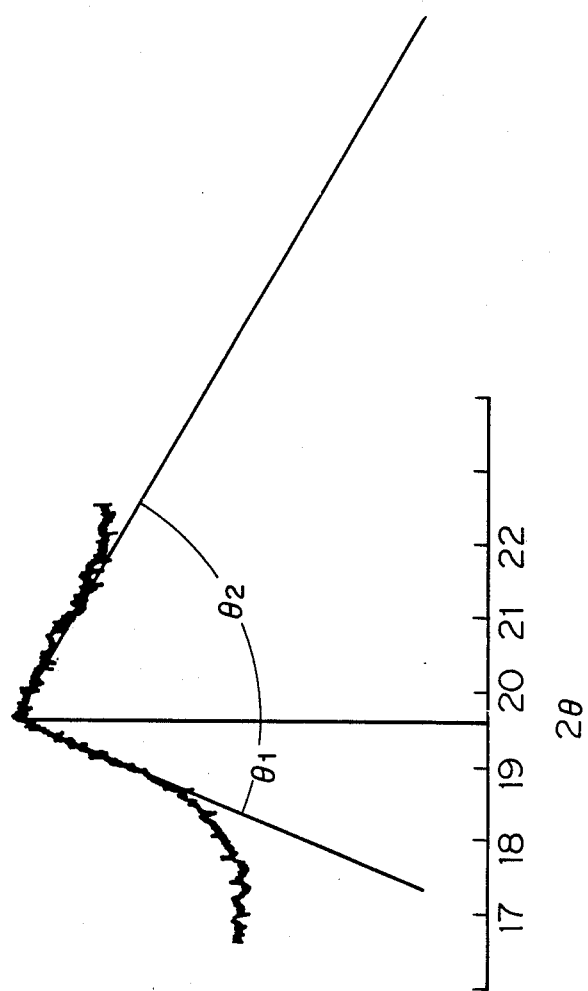
FIG. 2 is an enlarged graph of the diffraction peak in the vicinity of d=4.5 Å in the X-ray diffraction spectrum shown in FIG. 1, which illustrates the determination of $\theta_1$ and $\theta_2$ for calculation of the lamination asymmetry index (Is).

In the synthetic lamellar magnesium phyllosilicate of the present invention, although the above-mentioned layers are laminated in parallel to one another, a certain peculiar irregularity is observed at relative positions of the respective layers. FIG. 2 is an enlarged graph of the diffraction peak in the vicinity of d=4.5 Å in the X-ray diffraction spectrum shown in FIG. 1. From FIG. 2, it is seen that this peak is an asymmetric peak in which rising on the small diffraction angle side (the side of smaller 2θ) is relatively sharp but inclination is gradual on the large diffraction angle side (the side of larger 2θ). In the spectrum in which lamination of layers is regular, this peak is symmetric, and the above-mentioned asymmetric peak indicates the presence of a certain irregularity at relative positions of the respective layers.

In the instant specification, the lamination asymmetry index (Is) of magnesium phyllosilicate is defined as follows. An X-ray diffraction chart as shown in FIG. 2 is obtained according to the method described in the examples given hereinafter. With respect to the peak of d=4.5–4.6 Å, the tangent a to the maximum inclination of the peak on the small diffraction angle side and the tangent b to the maximum inclination of the peak on the large diffraction angle side are drawn, and the perpendicular c is drawn from the intersection point of the tangents a and b. The angle $\theta_1$ between the tangent a and perpendicular c and the angle $\theta_2$ between the tangent b and perpendicular c are determined. The lamination asymmetry index (Is) is calculated according to the following formula:

$$Is = \tan\theta_2 / \tan\theta_1 \quad (2)$$

When the peak is completely symmetric, this index (Is) is 1, and the more asymmetric is the peak, the larger is the value Is.

The synthetic lamellar magnesium phyllosilicate of the present invention has a novel irregular lamination structure in which the lamination asymmetry index (Is) is at least 3.0 and preferably in the range of from 3.5 to 6.0. By dint of this peculiar structure, the phyllosilicate of the present invention exerts a peculiar function of emulsifying water and oil.

Table A given below shows lamination asymmetry indexes (Is) of magnesium phyllosilicates prepared by using various starting silica materials and subjecting them to a hydrothermal treatment together with the starting magnesium material. Moreover, Table A shows the states observed when these magnesium phyllosilicates are added to a system comprising liquid paraffin and water. Incidentally, in column "Oil Phase-Water Dispersion State" in Table A, "oil phase" indicates that the magnesium phyllosilicate is completely contained in the oil phase, and "emulsification" indicates that the magnesium phyllosilicate is present in the vicinity of the interface between the oil phase and the water phase and a state of emulsion of oil and water is produced in this region.

TABLE A

| Silica Source | Reaction Molar Ratio ($SiO_2/MgO$) | Lamination Asymmetry Index (Is) | Oil Phase-Water Phase Dispersion State |
|---|---|---|---|
| silica flower | 4/3 | 2.4 | oil phase |
| colloidal silica | 4/3 | 2.2 | oil phase |
| gas phase method silica | 4/3 | 2.5 | oil phase |
| active silicic acid derived from acid clay produced at Nakajo | 4/3 | 4.3 | emulsification |
| active silicic acid derived from acid clay produced at Odo | 4/3 | 3.5 | emulsification |
| active silicic acid derived from acid clay produced at Nakajo | 4/4 | 4.0 | emulsification |
| active silicic acid derived from acid clay produced at Odo | 4/5 | 4.0 | emulsification |

From the results shown in Table A, it will be readily understood that although in each of magnesium phyllosilicates synthesized by using ordinary amorphous silica as the starting material the lamination asymmetry index (Is) is smaller than 3.0, magnesium phyllosilicate having a lamination asymmetry index (Is) of at least 3.0 can be obtained if active silicic acid or active aluminosilicic acid prepared by an acid treatment of a clay mineral is used as the starting material, and that the lamination asymmetry index of at least 3.0 is very critical for the function of emulsifying oil and water. Incidentally, if the lamination asymmetry index (Is) is too large, the stability of the oil-water emulsifying and dispersing property is degraded with the lapse of time and the magnesium phyllosilicate is gradually transferred into the water phase. Accordingly, in view of the stability of the characteristic properties with the lapse of time, it is preferred that the value Is be smaller than 8.0, especially smaller than 6.0.

The synthetic lamellar magnesium phyllosilicate of the present invention can be clearly distinguished from natural lamellar phyllosilicates. In natural phyllosilicates, since a number of basic three-layers structures are accumulated in the direction of the axis c, an X-ray diffraction peak peculiar to plane (001) appears at d=9–15 Å. However, in the synthetic lamellar magnesium phyllosilicate of the present invention, a clear diffraction peak is not observed at d=9–15 Å. This means that there is no lamination of layers in the direction of the axis C. In natural phyllosilicates, even though the peak in the vicinity of d=4.5 Å is asymmetric more or less, the lamination asymmetry index (Is) is smaller than 2 in most cases.

The synthetic lamellar magnesium phyllosilicate of the present invention has such a large specific surface area and such a high Methylene Blue decolorizing power as not observed in any of known natural and synthetic phyllosilicates at all. Namely, the magnesium phyllosilicate of the present invention has such a large BET specific surface area of at least 300 m$^2$/g, especially at least 500 m$^2$/g, and such a high Methylene Blue decolorizing power as at least 100 ml/g, especially at least 250 ml/g, as measured according to JIS K-1470. It is considered that the reason why the synthetic lamellar phyllosilicate of the present invention has such large specific surface area and high dye absorbing property as described above is that the lamination of the layers has a certain irregularity and other substance is easily included between two adjacent layers.

Preparation Process

In the process of the present invention, active silicic acid or active aluminosilicic acid prepared by an acid treatment of a clay mineral is used as the starting silicic acid component. This active silicic acid or aluminosilicic acid shows, in the synthesis of lamellar magnesium phyllosilicate, characteristics not possessed by other starting silicic acid components. First of all, the active silicic acid or active aluminosilicic acid is a gel of amorphous silicic acid or aluminosilicic acid having a very large specific surface area, ordinarily a BET specific surface area of 50 to 300 m$^2$/g, and is advantageous in that the reactivity is prominently high. Moreover, this active silicic acid or aluminosilicic acid is quite different from ordinary gel-like silica in that it has a fine microstructure suitable for the synthesis of a lamellar silicate type mineral having the above-mentioned microstructure. Generally, a clay mineral has a two-layer or three-layer base structure comprising a layer of a tetrahedron of $SiO_4$ and a layer of an octahedron of $AlO_6$ or the like bonded in the form of a laminate, and these base structures are laminated to form a multi-layer structure. If clay mineral having such a structure is treated with an acid, the $AlO_6$ octahedron layer is extracted as a soluble salt by the reaction with the acid and its crystal structure is substantially destroyed, but the $SiO_4$ tetrahedron layer retains a fine layer structure and constitutes a main portion of active silica.

As pointed out hereinbefore, the lamellar magnesium phyllosilicate has a three-layer base structure comprising a layer of an octahedron of $MgO_6$ sandwiched with two layers of a tetrahedron of $SiO_4$. This magnesium phyllosilicate is in common with the acid-treated clay mineral in that the $SiO_4$ tetrahedron layer is bonded lamellarly to the $MgO_6$ or $AlO_6$ octahedron layer, and also in common with the starting clay in that a layer of a tetrahedron of $SiO_4$ is present.

According to the present invention, by using the above-mentioned active silicic acid or active aluminosilicic acid as the starting material, synthetic magnesium phyllosilicate having the above-mentioned microstructure and large specific surface area and adsorbing property can be easily obtained, and it is considered that the reason is that because of the presence of laminar silica as the base component of active silicic acid or active aluminosilicic acid, rearrangement to magnesium phyllosilicate having a fine layer-structure can be facilitated while retaining the skeleton shell of laminar silica.

In the present invention, as the clay material, there are preferably used a clay mineral of the smectite group, a clay mineral of the montmorillonite group such as such as acid clay, bentonite, sub-bentonite or fuller's earth, beidellite, saponite, nontronite and a mixture of two or more of them. Moreover, other clay minerals, for example, a clay mineral of the kaolin group such as kaolin or halloysite and a chain structure clay mineral such as attapulgite, sepiolite or palygorskite, can be used. For example, kaolin has no reactivity with an acid as it is, but if this is converted to metakaolin by calcination, it can be easily reacted with an acid.

It is preferred that the acid treatment of the mineral clay is carried out to such an extent that the X-ray diffraction peak of the plane index (001) of the clay mineral substantially disappears and the $Al_2O_3/SiO_2$ molar ratio of the product is within the range of from 1/11 to 1/99. The acid treatment may be carried out under known conditions. For example, as the acid, there may be used a mineral acid such as sulfuric acid, hydrochloric acid or nitric acid or an organic acid such as benzene-sulfonic aid, toluene-sulfonic acid or acetic acid. Ordinarily, a mineral acid such as sulfuric acid is used. The method of contact of the clay mineral with the acid is not particularly critical, and for example, there can be adopted a slurry activation method in which the clay is contacted with the acid in the slurry state, a granular activation method in which the granulated clay is subjected to solid-liquid contact with the acid, and a dry activation method in which a mixture of the clay and acid is reacted in the dry state (within particles) and a salt formed as a by-product is then extracted. The amount used of the acid is changed according to the acid treatment conditions, but the acid is ordinarily used in such an amount that the $Al_2O_3/SiO_3$ molar ratio in the product is within the above-mentioned range and $Fe_2O_3$, MgO and other basic components such as an alkali metal component are substantially removed. For example, in case of the dry activation method, the acid treatment is carried out by using an acid or an aqueous solution of an acid in an amount of 0.3 to 1.5 equivalents, especially 0.6 to 1.2 equivalents, to the basic components in the mineral. The reaction conditions are selected within temperatures of 60° to 30020 C. and reaction times of 10 to 600 minutes so that the above-mentioned requirements are satisfied. Extraction of the soluble basic component from the reaction product is carried out in an aqueous medium having a pH value smaller than 1 so as to prevent advance of the hydrolysis.

It is preferred that the particle size of the acid-treated product of the clay mineral be as fine as possible. More specifically, it is preferred that before the hydrothermal treatment, the particle size of the acid-treated product of the clay mineral be adjusted so that particles having a particle size smaller than 5 $\mu$ occupy at least 20% by weight, especially at least 30% by weight, of the total particles and particles having a particle size larger than 20 $\mu$ occupy less than 30% by weight, especially less than 10% by weight, of the total particles.

As the starting magnesium component, there can be used an oxide or hydroxide of magnesium or a compound capable of forming said oxide or hydroxide under the reaction conditions. As a typical instance of this compound, there can be mentioned a magnesium alkoxide. There may be adopted a method in which a magnesium salt is decomposed in situ to magnesium hydroxide and this magnesium hydroxide is used for the reaction. However, in order to obtain magnesium phyllosilicate having high quality, incorporation of water-soluble salts into the reaction system should be avoided. An oxide or hydroxide of magnesium is preferred as the starting material.

In the process of the present invention, it is preferred that active silicic acid or active aluminosilicate ($SiO_2$) and the starting magnesium component (MgO) be used in substantially stoichiometric amounts for the reaction. More specifically, the $MgO/SiO_2$ molar ratio is preferably ¾, and it is permissible that the $MgO/SiO_2$ molar ratio may be changed within the range of from 2/4 to 6/4.

At the hydrothermal treatment, both the starting materials are formed into an aqueous slurry having a solid content of 2 to 30% by weight so that stirring of the reaction mixture is possible and the reaction can be performed homogeneously, and this aqueous slurry is charged in an autoclave and the hydrothermal reaction is carried out. The reaction is carried out at a temperature of 110° to 200° C., and the reaction pressure is maintained at a level of 0.5 to 15.5 kg/cm² gauge. The reaction time depends on the temperature and pressure, but it is preferred that the reaction time be 0.5 to 10 hours. It is preferred that the reaction be carried out under pressure, but magnesium phyllosilicate can be obtained even by carrying out the hydrothermal treatment under no pressurization.

The product is subjected to a post treatment such as water washing, drying, pulverization or classification according to need.

Uses

By dint of the above-mentioned micro-structure and characteristics, the synthetic lamellar magnesium phyllosilicate of the present invention can be applied to various uses.

For example, since the magnesium phyllosilicate has a function of emulsifying oil and water, it can be used as an inorganic emulsifier. If this synthetic magnesium phyllosilicate is incorporated in an amount of 0.1 to 5 parts by weight per 100 parts by weight of a water-oil system, an emulsion can be easily formed. In this case, if the proportion of oil is small, an oil-in-water type (o/w type) emulsion is formed, and if the proportion of oil is large, a water-in-soil type (w/o type) emulsion is formed. Accordingly, this magnesium phyllosilicate can be used as a cosmetic base for various milky lotions, creams and lotions, and it can also be used as a base or emulsifier for polishing waxes and cleaning waxes, detergents, pitch control agents for papers and pulps, and other emulsions.

Moreover, since the synthetic magnesium phyllosilicate of the present invention has a large specific surface area and a high dye adsorbing property, it can be used as a waste water treating agent for adsorbing and removing dyes and pigments from various waste waters. Furthermore, the synthetic magnesium phyllosilicate of the present invention can be used as a filler for an information recording paper and as a color developer for a pressure-sensitive recording paper.

The present invention will now be described in detail with reference to the following examples that by no means limit the scope of the invention.

The test methods adopted in the examples will now be described.

1. X-Ray Diffratometry

The apparatus used for the X-ray diffractometry was one supplied by Rigaku Denki K.K. (equipped with X-ray generating device Model 4036A1, goniometer Model 2125D1 and counter Model 5071). The diffraction conditions were as follows:
Target: Cu
Filter: Ni
Detector: SC
Voltage: 35 KVP
Current: 15 mA
Count full scale: 8000 c/s
Time constant: 1 second
Scanning speed: 2°/min
Chart speed: 2 cm/min
Emission angle: 1°
Slit width: 0.3 mm
Glancing angle: 6°

2. Determination of Lamination Asymmetry Indexes (Is)

A. X-ray Diffraction Conditions
Target: Cu
Filter: Ni
Detector: SC
Voltage: 40 KVP
Current: 20 mA
Count full scale: 4000 c/s
Time constant: 2 seconds
Scanning speed: 0.5°/min
Chart speed: 0.5 cm/min
Emission angle: 1°
Slit width: 0.3 mm
Glancing angle: 6°
Measurement diffraction angle range: 17° to 22° ($2\theta$)
Adoptable conditions are not limited to those described above. The voltage and current and other conditions may be set so that the peak height from the base line is in the range of from 2 to 5 cm.

B. Calculation of Lamination Asymmetry Index (Is)

On the small angle and large angle sides of the peak at the diffraction angle ($2\theta$) of 19.5°–19.7°, peak tangents (a and b) are drawn so that the absolute value of each gradient is largest. The perpendicular c is drawn from the intersection of the peak tangent a on the small diffraction angle side and the peak tangent b on the large diffraction angle side, and the angle $\theta_1$ formed by the tangent a and perpendicular c and the angle $\theta_2$ formed by the tangent b and the perpendicular c are determined. The lamination asymmetry index (Is) is calculated according to the following formula:

$$Is = \tan\theta_2/\tan\theta_1$$

3. BET Specific Surface Area (SA)

The specific surface area of each powder was measured according to the so-called BET method utilizing adsorption of nitrogen gas. This method is described in detail in S. Brunauer, P. H. Emmett and E. Teller, J. Am. Chem. Soc., Volume 60, 309 (1938).

In the examples, 0.5 to 0.6 g of a sample dried at 150° C. in advance was charged in a weighing bottle and dried for 1 hour in a thermostat drier maintained at 150° C., and immediately, the weight was precisely measured. The sample was charged in an adsorption sample tube and heated at 200° C., and the tube was evacuated so that the vacuum degree in the tube was $10^{-4}$ mmHg. After natural cooling, the sample tube was placed in liquefied nitrogen maintained at about −196° C. and the amount adsorbed of $N_2$ gas was measured at 4 to 5 points where the value of $pN_2/po$ was in the range of from 0.05 to 0.30 ($pN_2$ stands for the nitrogen gas pressure and po stands for the atmospheric pressure at the time of the measurement). The amount adsorbed of $N_2$ gas, from which the dead volume was subtracted, was converted to the adsorption amount at 0° C. under 1 atmosphere, and the adsorption amount was substituted in the BET equation to obtain Vm (cc/g) (the amount absorbed of nitrogen gas necessary for formation of a monomolecular layer on the sample surface). The specific surface area was calculated according to the following formula:

$$SA\ (m^2/g) = 4.35 \times Vm$$

4. Measurement of Methylene Blue Decolorizing Power

The Methylene Blue decolorizing power was determined according to the testing method of powdered active carbon of JIS K-1470.

5. Oil Phase-Water Phase Dispersion State of Powder

A tablet bottle of glass having a capacity of 50 ml was charged with 20 g of pure water and 20 g of liquid paraffin (first class reagent), and 0.4 g of a sample was added. The mixture was dispersed for 15 minutes by a paint shaker (supplied by Red Devil Co.). Then, the mixture was allowed to stand still at room temperature for 24 hours, and the dispersion state of the sample was observed.

Example 1

Acid clay produced at Nakajo-machi, Niigata prefecture, Japan was roughly pulverized and molded in a linear form having a diameter of 3 mm, and 250 g of the so-molded clay was mixed with sulfuric acid in an amount corresponding to 3.5 times the total gram equivalents (1.14 gram equivalents/100 g of the dry clay) of basic metal components contained in the clay, such as aluminum, magnesium, calcium, iron, sodium, potassium and titanium, that is, 700 ml of 34% sulfuric acid. The mixture was heated on a water bath maintained at 85° C. for 15 hours to effect a heat treatment. Water washing was carried out by filtration to obtain a cake. A small amount of the cake was dried at 110° C., pulverized and subjected to the quantitative analysis. It was found that the $SiO_2$ content was 92.7% (based on the product dried at 110° C.). The obtained cake was charged in a pot mill and water was added, and wet pulverization was carried out by using flint balls to obtain a slurry having an $SiO_2$ content of 15% (the first step was completed).

The, 200 g of the obtained slurry (30 g of $SiO_2$) and 22 g of magnesium hydroxide (first class reagent) were charged in an autoclave having an inner capacity of 1 liter, and 370 g of water was further added and hydrothermal synthesis reaction was carried out at 160° C. under agitation at 500 rpm for 5 hours. After cooling, the reaction product was taken out and water was separated by filtration, and the residue was dried at 130° C. The dried product was pulverized by a small desk sample mill to obtain a white fine powder (the second step was completed).

From the results of the X-ray diffractometry, it was found that the product was intended lamellar magnesium phyllosilicate.

The lamination asymmetry index (Is), BET specific surface area, Methylene Blue decolorizing power and oil phase-water phase dispersion state of the product are shown in Table 1.

Example 2

Acid clay (having a water content of 32.4%) produced at Odo, Shibata city, Niigata prefecture, Japan was roughly pulverized, and 3 kg of 25% sulfuric acid was added to 740 g of the roughly pulverized clay. The mixture was heated at 95° C. for 10 hours and the liquid was removed by filtration, and 3 kg of 25% sulfuric acid was added to the residue again and the mixture was heated at 95° C. for 10 hours to complete a heat treatment. Water washing was carried out by filtration to obtain a cake. A small amount of the cake was dried at 10° C. and subjected to the determinative analysis. It was found that the $SiO_2$ content was 91.5% (based on the product dried at 110° C.). The obtained cake was charged in a pot mill and water was added, and the mixture was wet-pulverized by using flint balls to obtain a slurry having an $SiO_2$ content of 15% (the first step was completed).

Then, 200 g of the so-obtained slurry (30 g of $SiO_2$) and 22 g of magnesium hydroxide (first class reagent) were charged in an autoclave having a capacity of 1 liter, and 370 g of water was added and hydrothermal synthesis reaction was carried out at 160° C. under agitation at 500 rpm for 5 hours. After cooling, the reaction product was taken out and water was separated by filtration, and the residue was dried at 130° C. and pulverized by a small desk sample mill to obtain a white fine powder (the second step was completed).

From the results of the X-ray diffractometry, it was found that the product was intended lamellar magnesium phyllosilicate.

The lamination asymmetry index (Is), BET specific surface area, Methylene Blue decolorizing power and oil phase-water phase dispersion state are shown in Table 1.

Example 3

An autoclave having a capacity of 1 liter was charged with 200 g of the slurry obtained at the first step of Example 1 (30 g of $SiO_2$) and 30 g of magnesium hydroxide (first class reagent), and 370 g of water was added and hydrothermal synthesis reaction was carried out at 160° C. under agitation at 500 rpm for 5 hours. After cooling, the reaction product was taken out and water was separated by filtration, and the residue was dried at 130° C. The dried product was pulverized by a small desk sample mill to obtain a white fine powder.

From the results of the X-ray diffractometry, it was found that the product was intended lamellar magnesium phyllosilicate.

The lamination asymmetry index (Is), BET specific surface area, Methylene Blue decolorizing power and oil phase-water phase dispersion state of the product are shown in Table 1.

Example 4

An autoclave having a capacity of 1 liter was charged with 200 g of the slurry obtained at the first step of Example 2 (30 g of $SiO_2$) and 35 g of magnesium hydroxide (first class reagent), and 370 g of water was added and hydrothermal synthesis reaction was carried out at 160° C. under agitation at 500 rpm for 5 hours. After cooling, the reaction product was taken out and water was separated by filtration, and the residue was dried at 130° C. The dried product was pulverized by a small desk sample mill to obtain a white fine powder.

From the results of the X-ray diffractometry, it was found that the product was lamellar magnesium phyllosilicate.

The lamination asymmetry index (Is), BET specific surface area, Methylene Blue decolorizing power and oil phase-water phase dispersion state of the product are shown in Table 1.

Comparative Example 1

An autoclave having a capacity of 1 l was charged with 32 g of ferrosilicon dust produced as a by-product in the production of ferrosilicon and 22 g of magnesium hydroxide (first class reagent), and 550 g of water was added to form a slurry. Hydrothermal synthesis reaction was carried out at 160° C. under agitation at 500 rpm for 5 hours. After cooling, the reaction product was taken out and water was removed by filtration. The residue was dried at 130° C. The dried product was pulverized by a small desk sample mill to obtain a grayish white fine powder.

From the results of the X-ray diffractometry, it was found that the product was lowly crystalline magnesium silicate.

The lamination asymmetry index (Is), BET specific surface area, Methylene Blue decolorizing power and oil phase-water phase dispersion state of the product are shown in Table 1.

Comparative Example 2

An autoclave having a capacity of 1 l was charge with 10 g of commercially available colloidal silica (Snowtex 30 supplied by Nissan Kagaku K.K.) and 22 g of magnesium hydroxide (first class reagent), and 470 g of water was added to form a slurry. Hydrothermal synthesis reaction was carried out at 160° C. under agitation at 500 rpm for 5 hours. After cooling, the reaction product was taken out, and water was separated by filtration. The residue was dried at 130° C. and pulverized by a desk sample mill to obtain a fine white powder.

From the results of the X-ray diffractometry, it was found that the product was lowly crystalline magnesium silicate.

The lamination asymmetry index (Is), BET specific surface area, Methylene Blue decolorizing power and oil phase-water phase dispersion state of the product are shown in Table 1.

Comparative Example 3

An autoclave having a capacity of 1 l was charged with 30 g of commercially available gas phase method silica (Aerosil 200 supplied by Nippon Aerosil K.K.) and 22 g of magnesium hydroxide (first class reagent), and 550 g of water was added to form a slurry. Hydrothermal synthesis reaction was carried out at 160° C. under agitation at 500 rpm for 5 hours. After cooling, the reaction product was taken out, and water was separated by filtration. The results was dried out at 130° C. and the dried product was pulverized by a small desk mill to obtain a fine white powder.

From the results of the X-ray diffractometry, it was found that the product was lowly crystalline magnesium silicate.

The lamination asymmetry index (Is), BET specific surface area, Methylene Blue decolorizing power and oil phase-water phase dispersion state of the product are shown in Table 1.

TABLE 1

| | Lamination Asymmetry Index (Is) | BET Specific Surface Area ($m^2/g$) | Methylene Blue Decolorizing Power (ml/g) | Oil Phase-Water Phase Dispersion State |
|---|---|---|---|---|
| Example 1 | 4.3 | 526 | 280 | emulsification |
| Example 2 | 3.5 | 461 | 230 | emulsification |
| Example 3 | 4.0 | 503 | 250 | emulsification |
| Example 4 | 4.0 | 382 | 170 | emulsification |
| Comparative Example 1 | 2.4 | 210 | 50 | oil phase |
| Comparative Example 2 | 2.2 | 275 | 80 | oil phase |
| Comparative Example 3 | 2.5 | 286 | 80 | oil phase |

We claim:

1. Synthetic lamellar magnesium phyllosilicate, which has as the main component a composition represented by the following formula:

$$Mg_3Si_4O_{10}(OH)_2 \cdot nH_2O$$

wherein n is a number of up to 5, and has X-ray diffraction peaks at spacings of 4.5–4.6 Å, 2.5–2.6 Å and 1.5–1.6 Å, wherein the lamination asymmetry index (Is) defined by the following formula:

$$Is = \tan \theta_2 / \tan \theta_1$$

wherein
$\theta_1$ stands for the angle formed by the peak perpendicular and the peak tangent on the small diffraction angle side in the X-ray diffraction peak at a spacing of 4.5–4.6 Å, and
$\theta_2$ stands for the angle formed by the peak perpendicular and the peak tangent on the large diffraction angle side in said X-ray diffraction peak, is in the range of from 3.5 to 6.0, the BET specific surface area is at least 300 $m^2/g$ and the Methylene Blue decolorizing power (JIS K-1470) is at least 100 ml/g, said lamellar magnesium phyllosilicate being further characterized by its ability to stably emulsify water and oil, said emulsifying ability being determined by adding 0.4 gram of the phyllosilicate to a mixture of 20 grams of pure water and 20 grams of liquid paraffin, dispersing the resulting mixture for 15 minutes and allowing the mixture to stand still at room temperature for 24 hours, said lamellar magnesium phyllosilicate being obtained by subjecting an acid clay mineral belonging to the montmorillonite group to an acid treatment to such an extent that the X-ray diffraction peak of the plane index (001) of the clay mineral substantially disappears and the $Al_2O_3/SiO_2$ molar ratio of the acid-treated product is within the range of from 1/11 to 1/99 and subjecting the acid-treated product of the clay mineral and an oxide or hydroxide of magnesium or a compound capable of forming said oxide or hydroxide under reaction conditions to a hydrothermal treatment at an MgO/SiO$_2$ molar ratio of from 2/4 to 6/4 at a temperature of 110° to 200° C.

2. Synthetic lamellar magnesium phyllosilicate as set forth in claim 1, wherein n is a number of from 0.5 to 3.

3. Synthetic lamellar magnesium phyllosilicate as set forth in claim 1, wherein the BET specific surface area is at least 500 m$^2$/g.

4. Synthetic lamellar magnesium phyllosilicate as set forth in claim 1, wherein the Methylene Blue decolorizing power is at least 250 ml/g.

5. A process for the preparation of synthetic lamellar magnesium phyllosilicate, which comprises (i) subjecting an acid clay mineral belonging to the montmorillonite group to an acid treatment to such an extent that the X-ray diffraction peak of the plane index (001) of the clay mineral substantially disappears and the Al$_2$O$_3$/SiO$_2$ molar ratio of the acid-treated product is within the range of from 1/11 to 1/99, the acid treatment being carried out using an acid or an aqueous solution of an acid in an amount of 0.3 to 1.5 equivalents to the basic components in the mineral, reacting the mineral with the acid at a temperature of 60° to 300° C. for 10 to 600 minutes and extracting the soluble basic component from the reaction product in an aqueous medium having a pH value smaller than 1 (ii) adjusting the particle size of the acid-treated product of the clay material so that particles having a particle size smaller than 5 μ occupy at least 20% by weight of the total particles and particles having a particle size larger than 20 μ occupy less than 30% by weight of the total particles, and (iii) subjecting the acid-treated product of the clay mineral and an oxide or hydroxide of magnesium or a compound capable of forming said oxide or hydroxide under reaction conditions to a hydrothermal treatment at an MgO/SiO$_2$ molar ratio of from 2/4 to 6/4 at a temperature of 110° to 200° C. to form a synthetic lamellar phyllosilicate having as the main component a composition represented by the formula $$Mg_3SiO_4O_{10}(OH)_2 \cdot nH_2O$$

wherein n is a number of up to 5, and having an X-ray diffraction peaks at spacings of 4.5–4.6 Å, 2.5–2.6 Å and 1.5–1.6 Å.

6. A process according to claim 5, wherein the acid-treated product of the clay mineral and the starting magnesium component are used in substantially stoichiometric amounts as SiO$_2$ and MgO for the hydrothermal treatment.

7. A process according to claim 5, wherein the hydrothermal treatment is carried out under a pressure of 0.5 to 15.5 kg/cm$^2$ gauge.

8. A process according to claim 5, wherein the hydrothermal treatment is conducted for 0.5 to 10 hours.

* * * * *

UNITED STATES PATENT AND TRADEMARK OFFICE
CERTIFICATE OF CORRECTION

PATENT NO. : 4,830,843

DATED : May 16, 1989

INVENTOR(S) : KOICHI USUI ET AL.

It is certified that error appears in the above-identified patent and that said Letters Patent is hereby corrected as shown below:

Claim 5, line 29 of the claim, "$Mg_3SiO_4O_{10}(OH)_2 \cdot nH_2O$" should read --$Mg_3Si_4O_{10}(OH)_2 \cdot nH_2O$--.

Signed and Sealed this

Third Day of April, 1990

Attest:

HARRY F. MANBECK, JR.

*Attesting Officer*      *Commissioner of Patents and Trademarks*